United States Patent
Greenbaum et al.

(10) Patent No.: US 9,222,888 B2
(45) Date of Patent: Dec. 29, 2015

(54) PULSE AMPLITUDE MODULATED CHLOROPHYLL FLUOROMETER

(75) Inventors: Elias Greenbaum, Knoxville, TN (US); Jie Wu, Knoxville, TN (US)

(73) Assignees: UT-Battelle, LLC, Oak Ridge, TN (US); University of Tennessee Research Foundation, Knoxville, TN (US)

( * ) Notice: Subject to any disclaimer, the term of this patent is extended or adjusted under 35 U.S.C. 154(b) by 649 days.

(21) Appl. No.: 13/438,562

(22) Filed: Apr. 3, 2012

(65) Prior Publication Data

US 2013/0256561 A1 Oct. 3, 2013

(51) Int. Cl.
*G01N 21/64* (2006.01)

(52) U.S. Cl.
CPC ........ *G01N 21/6486* (2013.01); *G01N 21/6428* (2013.01); *G01N 2201/0625* (2013.01)

(58) Field of Classification Search
CPC .............. G01N 21/64; G01N 21/6486; G01N 21/6428; G01N 21/03; G01N 21/031
USPC ........................................... 250/458.1–461.2
See application file for complete search history.

(56) References Cited

U.S. PATENT DOCUMENTS

| | | | |
|---|---|---|---|
| 5,323,010 A | 6/1994 | Gratton et al. | |
| 6,531,702 B1 * | 3/2003 | Mischler et al. | 250/339.12 |
| 6,563,122 B1 * | 5/2003 | Ludeker et al. | 250/458.1 |
| 2008/0032326 A1 * | 2/2008 | Greenbaum et al. | 435/34 |

OTHER PUBLICATIONS

Lefevre, F., et al., Algal Fluorescence Sensor Integrated Into a Microfluidic Chip for Water Pollutant Detection, Lab on a Chip, Dynamic Article Links, www.rsc.org/loc, The Royal Society of Chemistry 2012, pp. 787-793.
Podola et al., "Selective real-time herbicide monitoring by an array chip biosensor employing diverse microalgae", Journal of Applied Phycology, vol. 17, pp. 261-271 (2005).
Schreiber et al., "Chlorophyll fluorescence: new instruments for special applications", Photosynthesis: Mechanisms and Effects, vol. 5, pp. 4253-4258 (1998).
Bergmann et al., "Picosecond laser-fluorometer with simultaneous time and wavelength resolution for monitoring decay, spectra of photoinhibited Photosystem II particles at 277 K and 10K", Photosynthesis Research, vol. 58, pp. 303-310 (1998).
Search Report and Written Opinion from International Search Authority in PCT US2013/034370, pp. 1-12, mailed Jul. 9, 2013.

* cited by examiner

*Primary Examiner* — Casey Bryant
(74) *Attorney, Agent, or Firm* — Brinks Gilson & Lione (57) ABSTRACT

Chlorophyll fluorometry may be used for detecting toxins in a sample because of changes in micro algae. A portable lab on a chip ("LOAC") based chlorophyll fluorometer may be used for toxin detection and environmental monitoring. In particular, the system may include a microfluidic pulse amplitude modulated ("PAM") chlorophyll fluorometer. The LOAC PAM chlorophyll fluorometer may analyze microalgae and cyanobacteria that grow naturally in source drinking water.

22 Claims, 9 Drawing Sheets

DEP Electrodes for Particle Focusing

PULSE AMPLITUDE MODULATED CHLOROPHYLL FLUOROMETER

STATEMENT REGARDING FEDERALLY SPONSORED RESEARCH

This invention was made with government support under Contract No. DE-AC05-00OR22725 awarded by the U.S. Department of Energy. The government has certain rights in the invention.

BACKGROUND

The use of chlorophyll fluorescence measurements to examine photosynthetic performance and stress in algae and plants may be used in physiological and eco-physiological studies. Micro algae that grow in water may have a characteristic fluorescence signature. That signature may be altered if exposed to toxins. Fluorescence may also be used to study photosynthetic performance when coupled with noninvasive measurements such as absorption spectroscopy, gas analyses, and infrared thermometry. A microfluidic analytical device for an algal cytometer may be performed under a microscope. However, microfluidic cytometers generally use only one excitation light source and the output is voltage pulses as opposed to a time-resolved waveform for fluorescence intensity.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

DETAILED DESCRIPTION

The disclosed system is a lab on a chip ("LOAC") based chlorophyll fluorometer for environmental monitoring. In particular, the system may include a microfluidic pulse amplitude modulated ("PAM") chlorophyll fluorometer. The LOAC chlorophyll fluorometer may analyze microalgae and cyanobacteria that grow naturally in source drinking water. Toxicity assays may also be performed in seawater, including petroleum contaminants. Detection may be achieved by algal biosensors that grow naturally in source drinking waters using chlorophyll fluorescence measurement. Variable chlorophyll fluorescence may be used to determine the physiological health of algae. Toxins may change the shape of the fluorescence curve to determine their presence in source waters.

Figure 1:
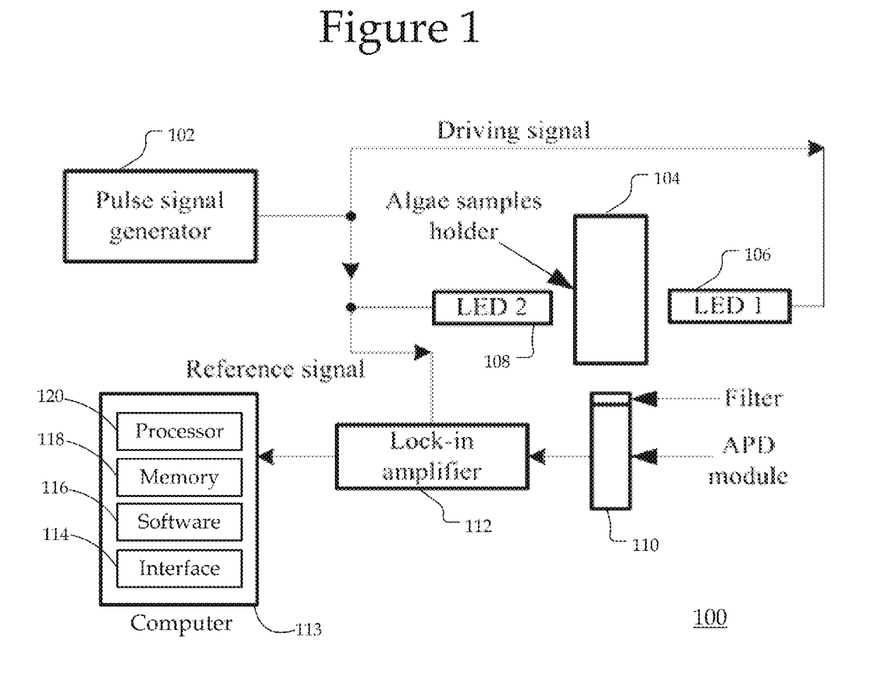
FIG. 1 is an exemplary diagram illustrating a lab on a chip ("LOAC") pulse amplitude modulated ("PAM") fluorometer.

FIG. 1 is an exemplary diagram illustrating a lab on a chip ("LOAC") pulse amplitude modulated ("PAM") fluorometer. The system 100 illustrates an exemplary embodiment for an LOAC PAM fluorometer. The LOAC PAM fluorometer may process both microliter sample and single cell in real time. Since it is a LOAC, the device may have a relatively small form factor that may be manufactured in large quantities.

The system 100 includes a pulse signal generator 102 that outputs a driving signal. The driving signal is an input to the light emitting diodes ("LED") 106, 108. The LEDs 106, 108 are light sources to an algae samples holder 104. The algae holder 104 is further described with respect to FIG. 3. The photodetector 110 may include a filter and measures changes to the algae in the holder 104 as a result of the LEDs 106, 108. The photodetector module 110 may be a photodiode, or a highly sensitive semiconductor electronic device that utilizes the photoelectric effect to convert light to electricity, such as an avalanche photodiode (APD), or photomultiplier.

The photodetector module 110 outputs to a lock-in amplifier 112. In one embodiment, the lock in amplifier 112 locks into a particular frequency of the modulated signal. The lock-in amplifier 112 may be referred to as a phase-sensitive detector and may be a type of amplifier that can extract a signal with a known carrier wave from a noisy environment. The lock-in amplifier 112 may convert the signal's phase and amplitude to a direct current voltage signal or a time-varying low-frequency signal. The device may be used to measure phase shift. The lock-in amplifier 112 transmits a reference signal to the computer 113.

In one embodiment, the LEDs 106, 108 may include blue 30° 5 mm LEDs with a center wavelength of 470 nanometer that provide actinic light sources. The LEDs may be driven by a signal generator 102, such as a 50 MHz Single-Channel PLL Pulse Function Generator in one embodiment. The emitted fluorescence may be collected by detector 110, such as an APD module after filtering through a bandpass filter (shown as part of the detector 110) with center wavelength at 685 nanometers that may include F-Bandpass Interference Filters in one embodiment. The voltage output of the detector 110 may be amplified by a lock-in amplifier 112 such as a Dual Phase DSP Lock-in Amplifier in one embodiment. Data from the amplifier may be sent to a computer 113.

Optical electronic systems may detect the fluorescence, using very narrow band pass filters (e.g. FIG. 2), and modulating the excitation signal of the fluorescence, and then having the lock in amplifier to synch into that modulated signal. Combining these techniques may enable signal analysis in even noisy environments. Further, given that the wavelength of fluorescence emission is around 685 nanometers there should be limited interference from the natural environment at that wavelength other than chlorophyll.

As described, the chlorophyll fluorescence measurement may be pulse amplitude modulated ("PAM") to provide additional information about the physiological health of a sample, such as algae. The pulse amplitude modulation ("PAM") fluorescence measurement may provide additional information about the physiological health of a sample, such as algae. In a conventional fluorescence measurement for a pure solution of chlorophyll, there may be an excitation source, along with a detector (e.g. photo diode detector or photodetector) adjacent the excitation source. The excitation light can be measured along with the fluorescence light. A measurement of the absolute number of photons coming in and the photons coming out may provide a quantum efficiency of fluorescence. Generally, the excitation intensity may be proportional to the light that is emitted. However, measuring the fluorescence of the chlorophyll in a living organism may be more complicated. Since photosynthesis is a process that is driven by light, when the incident light is too weak to drive the photosynthetic process, it is not bright enough to drive the electron transport chain to do the biochemistry of photosynthesis. Accordingly, the resulting fluorescence may be identical to a pure solution of chlorophyll molecules. With a dim light exciting the chlorophyll, there may be a straight, steady state light of fluorescence coming out.

Compared with conventional fluorescence measurements, PAM fluorometry may utilize a second light source, or alternatively, the same light source may be pulsed differently so that it mimics "two" light sources. With a second actinic light source that is bright, there may still be a weak first excitation light to measure fluorescence. Detecting the light that is emitted by the chlorophyll (~685 nm) may include choosing a wavelength of bright light that chlorophyll absorbs throughout a range from 400 to about 675 nanometers. Utilizing the excitation light in the blue range (bright light) to drive photosynthesis results in fluorescence that comes out at the red. The photodetector may need a narrow band pass filter for looking at a narrow range, such as around 685 nanometers. When the steady state low excitation light does not drive the photosynthetic process, there may still be a steady state fluorescence coming out from the chlorophyll pigment bed in the algae, similar to the pure chlorophyll solution noted above. Even though the same steady state low excitation light is maintained, if the second source is bright enough for photosynthesis, then the emitted fluorescence is not going to stay constant. The fluorescence that comes out may reflect the altering electron transport chain of the biochemical process. The variation of the fluorescence may be traced back to the ability of the plants to do photosynthesis and their physiological health.

The fluorescence pattern or signature that would be associated with healthy algae differs from the pattern or signature that is associated with algae that has been exposed to toxins or has been poisoned. As described, the lab on a chip design utilizes PAM chlorophyll fluorometry for detecting changes to the fluorescence pattern of algae which may identify toxins in a sample.

The pulsing of the actinic source may be at different non-685 nano meter wavelength. In one embodiment, a narrow band pass filter may lock around the 685 nanometers fluorescence wavelength. In other words, the signal that is emitted from the algae doing real photosynthesis is analyzed and the emitted light may be modulated and selected at the appropriate wavelength, which is then locked in for the analysis.

The computer 113 analyzes the results from the algae biosensors that grow naturally in source drinking waters using chlorophyll fluorescence measured with the photodetector or APD module 110. The computer 113 may also be referred to as an analyzer or processor for analyzing or processing the data from the photodetector 110. The computer or analyzer 113 may be a computing device for analyzing data from the photodetector that indicates algae growth or changes. The computer 113 may include a processor 120, a memory 118, software 116 and an interface 114. The computer 113 may be a separate component from the photodetector or APD module 110, or it may be combined as a single component or hardware device.

The interface 114 may communicate with the lock-in amplifier 112 or the APD module 110, or it may be an interface for user interaction with the computer 113. The interface 114 may include a user interface configured to allow a user and/or administrator to interact with any of the components of the computer 113. For example, a user may be able to update or review the results from the photodetector 110, as well as modify the methodology used by the computer 113 for analyzing the detected data.

The processor 120 in the computer 113 may include a central processing unit (CPU), a graphics processing unit (GPU), a digital signal processor (DSP) or other type of processing device. The processor 120 may be a component in any one of a variety of systems. For example, the processor 120 may be part of a standard personal computer or a workstation. The processor 120 may be one or more general processors, digital signal processors, application specific integrated circuits, field programmable gate arrays, servers, networks, digital circuits, analog circuits, combinations thereof, or other now known or later developed devices for analyzing and processing data. The processor 120 may operate in conjunction with a software program, such as code generated manually (i.e., programmed).

The processor 120 may be coupled with the memory 118, or the memory 118 may be a separate component. The software 116 may be stored in the memory 118. The memory 118 may include, but is not limited to, computer readable storage media such as various types of volatile and non-volatile storage media, including random access memory, read-only memory, programmable read-only memory, electrically programmable read-only memory, electrically erasable read-only memory, flash memory, magnetic tape or disk, optical media and the like. The memory 118 may include a random access memory for the processor 120. Alternatively, the memory 118 may be separate from the processor 120, such as a cache memory of a processor, the system memory, or other memory. The memory 118 may be an external storage device or database for storing recorded ad or user data. Examples include a hard drive, compact disc ("CD"), digital video disc ("DVD"), memory card, memory stick, floppy disc, universal serial bus ("USB") memory device, or any other device operative to store ad or user data. The memory 118 is operable to store instructions executable by the processor 120.

The functions, acts or tasks illustrated in the figures or described herein may be performed by the programmed processor executing the instructions stored in the memory 118. The functions, acts or tasks are independent of the particular type of instruction set, storage media, processor or processing strategy and may be performed by software, hardware, integrated circuits, firm-ware, micro-code and the like, operating alone or in combination. Likewise, processing strategies may include multiprocessing, multitasking, parallel processing and the like. The processor 120 is configured to execute the software 116.

The interface 114 may be a user input device or a display. The interface 114 may include a keyboard, keypad or a cursor control device, such as a mouse, or a joystick, touch screen display, remote control or any other device operative to allow a user to interact with the Computer 113. The interface 114 may include a display coupled with the processor 120 and configured to display an output from the processor 120. The display may be a liquid crystal display (LCD), an organic light emitting diode (OLED), a flat panel display, a solid state display, a cathode ray tube (CRT), a projector, a printer or other now known or later developed display device for outputting determined information. The display may act as an interface for the user to see the functioning of the processor 120 or the results of the data analysis. In particular, the interface 114 may allow a user to interact with the computer 113 to view results from the analysis of the detection by the photodetector 110.

The present disclosure contemplates a computer-readable medium that includes instructions or receives and executes instructions responsive to a propagated signal, so that a device connected to a network can communicate voice, video, audio, images or any other data over a network. The interface 114 may be used to provide the instructions over the network via a communication port. The communication port may be created in software or may be a physical connection in hardware. The communication port may be configured to connect with a network, external media, display, or any other components in system 100, or combinations thereof. The connection with the network may be a physical connection, such as a wired Ethernet connection or may be established wirelessly as discussed below. Likewise, the connections with other components of the system 100 may be physical connections or may be established wirelessly.

Any of the components in the system 100 may be coupled with one another through a network, including but not limited to the network 104. For example, the Computer 113 may be coupled with the ad/publisher server 106 through a network. Accordingly, any of the components in the system 100 may include communication ports configured to connect with a network.

The network or networks that may connect any of the components in the system 100 to enable communication of data between the devices may include wired networks, wireless networks, or combinations thereof. The wireless network may be a cellular telephone network, a network operating according to a standardized protocol such as IEEE 802.11, 802.16, 802.20, published by the Institute of Electrical and Electronics Engineers, Inc., or WiMax network. Further, the network(s) may be a public network, such as the Internet, a private network, such as an intranet, or combinations thereof, and may utilize a variety of networking protocols now available or later developed including, but not limited to TCP/IP based networking protocols. The network(s) may include one or more of a local area network (LAN), a wide area network (WAN), a direct connection such as through a Universal Serial Bus (USB) port, and the like, and may include the set of interconnected networks that make up the Internet. The network(s) may include any communication method or employ any form of machine-readable media for communicating information from one device to another. As discussed, the detected data from the detector 108 may be transmitted over a network, such as the network 104, as well as the analysis of that data from the computer 113.

Figure 2:
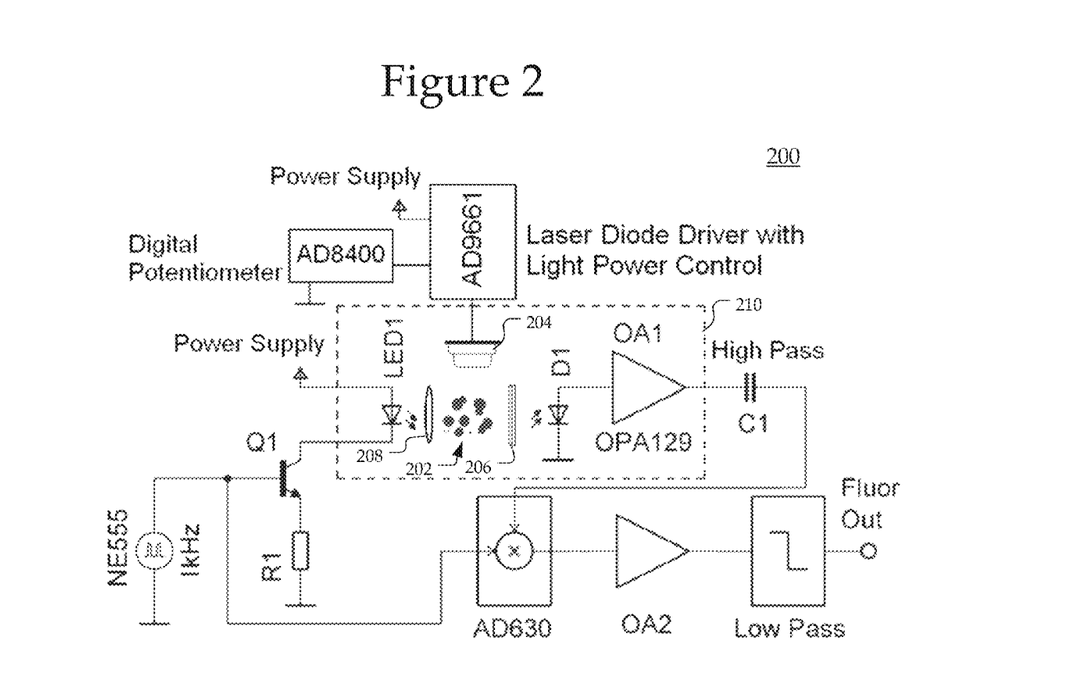
FIG. 2 is exemplary diagram illustrating another LOAC PAM fluorometer.

FIG. 2 is exemplary diagram illustrating another LOAC PAM fluorometer. In particular, the system 200 is an exemplary schematic illustration of the design layout of the optoelectronic components of the system. The detection area 210 includes a sample algae 202, LEDs 204, 208, and a photodetector 206. The algae 202 samples are exposed to a first and second LED 204, 208. The changes to the algae 202 and, in particular, the changes to the fluorescence signature of the algae 202 are detected by the photodetector 206. The actinic light 204 may be connected with or referred to as a laser diode driver with light power control (AD9661) that is connected with a power supply. A digital potentiometer (AD8400) is used for controlling the actinic light 204. The laser diode driver with light power control (AD9661) and digital potentiometer (AD8400) may be outside of the detection area 210.

The system 200 applies LOAC microfluidics technology to PAM chlorophyll fluorometry. Using PAM, fluorescence changes may be measured in real-time while the algae or cyanobacteria are performing photosynthesis, especially during the transition from darkness to light exposure (by turning on the actinic light source). It may differ from other fluorescence because of the presence of the actinic light source (in addition to the low intensity excitation light source used in other fluorescence. This may enable real-time data extraction of the presence of toxins in the water.

The system 200 is configured to handle a small sample size. For a given chlorophyll concentration, the strength of the fluorescence signal may be proportional to the sample size. Therefore, smaller sample volumes may imply fewer algae and a proportionally lower fluorescence signal. Electrofocusing techniques and optical design may be used for close positioning of the photodiode sensors to the microfluidics channels that include the algae 202 as further described with respect to FIG. 3. The system 200 may include optical and electronic signal filtering techniques to isolate the fluorescence emission line (e.g. 685 nanometer) including locking the electronic detectors to the modulated measuring beam for chlorophyll analysis. The NE555 may generate pulses which control the LED driver or transistor Q1 and trigger the multiplier chip AD630. R1 is a resistor that may be used to bias the LED driver circuit. AD630 may multiply the trigger signal and the amplified signal from the photodetector, allowing the passage of signals in sync with the trigger signal. OA stands for operational amplifier and there may be two OA's, which may be generic amplifiers. The low pass filer may remove the carrier frequency to obtain the DC to low frequency signal, while the high pass filter may remove low frequency noise.

Using optical narrow band filtering and lock in amplifying, along with concentrating the algae using the technique of electro-focusing or opto-electro kinetics may result in a signal to noise ratio that is sufficient for onboard lab on chip device. AC electro focusing or AC electro kinetics may be used for moving the algae in microchannels (as described with respect to FIGS. 3-9).

Figure 3:
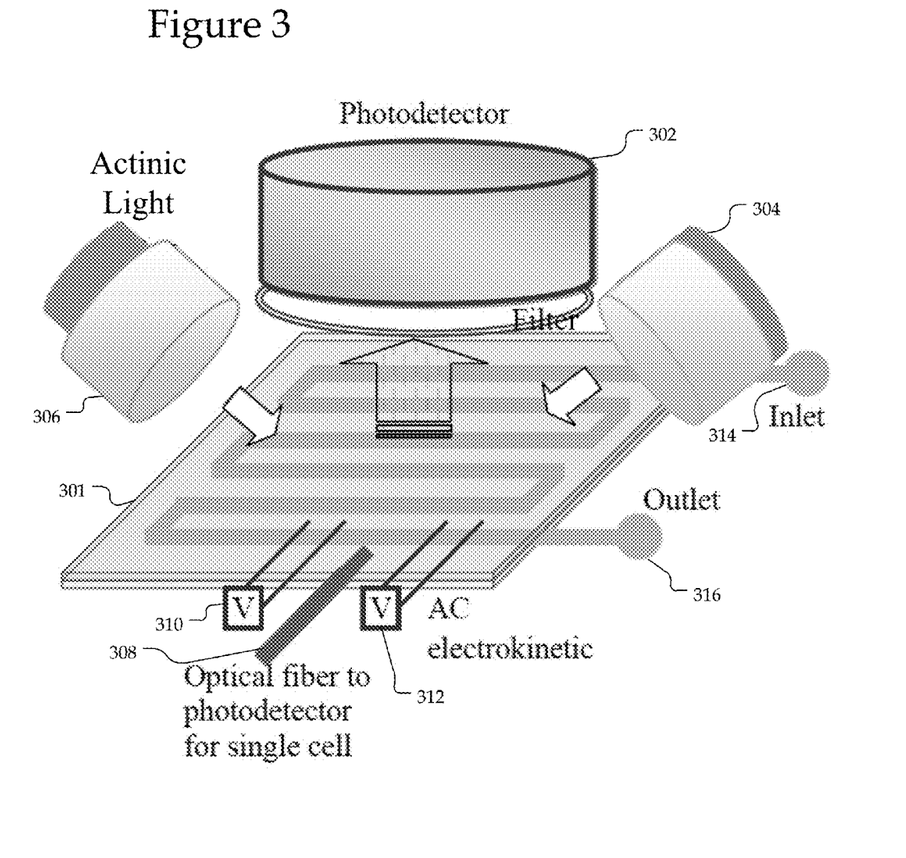
FIG. 3 is a diagram of the detection area.

FIG. 3 is a diagram of the detection area that includes the light sources 304, 306, and the photodetector 302, over the sample area 301. The photodetector 302 may be the APD module 110 from FIG. 1 or the photodetector 204 from FIG. 2. The photodetector 302 may include a filter. The photodetector 302 may include a device that converts light energy (photons) into electric current and may be a photodiode, an APD, or a photomultiplier. The light sources 304, 306 may include LEDs or actinic lights. The sample area 301 illustrates a meandering channel or microchannel through which the sample is passed. The channel inlet 314 is the source of the sample and it passes through the channel outlet 316. In particular, filtered sample water may be introduced into a meandering microchannel through the inlet 314. The microchannel may be built with transparent materials (e.g. poly-dimethyl-siloxane, polyimide, or glass) on a hard substrate. The two light sources 304, 306 or optical fibers (for measuring light and actinic light) as well as the photodetector 302 are positioned over the meandering channels. In one embodiment, the light sources 304, 306 and the photodetector 302 may be integrated into the top cover of the chip to create the LOAC design. The channels are further described below with respect to FIGS. 6-9.

Figure 4:
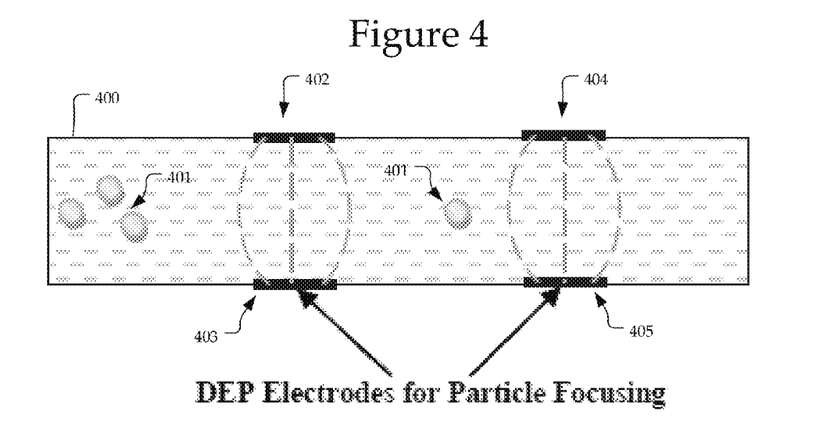
FIG. 4 is a diagram of an exemplary channel with particle focusing.

FIG. 4 is a diagram of an exemplary channel 400 with particle 401 focusing. A plurality of particles 401 as part of a sample are passed through the channel 400. The meandering channel may allow a relatively large volume (e.g. tens of microliters) of sample to be processed. Microelectrodes may be arranged in the channel path to concentrate the particles 401 for highly diluted samples. For example, the channel 400 includes electrodes 402-405 for concentrating particles 401. The concentration mechanism may utilize AC electrokinetics. Given an appropriate AC signal, particles 401 (e.g. algae) will be repelled from the electrodes (known as negative dielectrophoresis), which will stop their movement along the channel 400. Accordingly, by stopping movement, the particles 401 become concentrated. Since the operation is non-contact, particle passage can be resumed after the electric signal is turned off.

Figure 5:
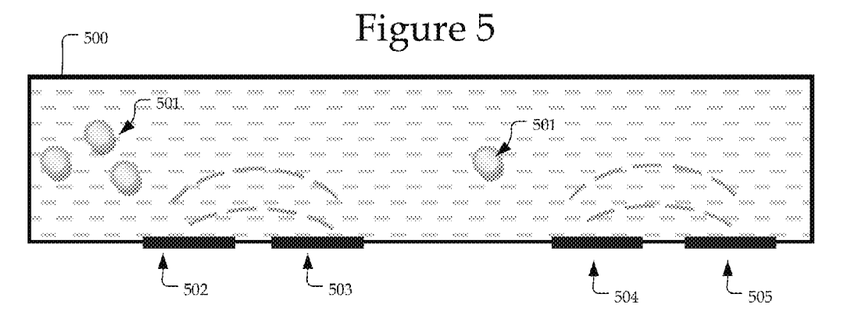
FIG. 5 is a diagram of another exemplary channel with particle focusing.

FIG. 5 is a diagram of another exemplary channel 500 with particle 501 focusing. A plurality of particles 501 as part of a sample are passed through the channel 500. The concentrating mechanism for the channel 500 in FIG. 5 is similar to the concentrating mechanism for the channel 400 in FIG. 4. Microelectrodes may be arranged in the channel 500 path to concentrate the particles 501 for highly diluted samples utilizing AC electrokinetics. For example, the channel 500 includes electrodes 502-505 for concentrating particles 501. Given an appropriate AC signal at the electrodes, the particles 501 may stop their movement or be directed along the channel 500. Analysis on the single cell level may be performed. An optic fiber may be embedded along the channel wall for extracting the fluorescence to a photodetector for analysis. The single cell may be held in place by dielectrophoretic electrodes (e.g. 502-505). Both large volume and single cell analysis may use the same set of measuring light and actinic light.

The design includes features to increase the photon flux into the photodetector. One feature is the use of meandering microchannels that folds into a larger area than that can be provided by a single channel width. The photodetector is positioned next to the microchannel, perpendicular to the chip surface, and its active (detection) area covers the total meandering part of the microchannel. The microchannels and their positioning is described with respect to FIGS. 3 and 6-9. Another feature for increasing the photon flux into the photodetector is that the microchannel may concentrate microalgae by locating microelectrodes close to the channel exit. The electrodes can repel microalgae when applied appropriate electric signals as described with respect to FIGS. 4-5. The algae may be stopped from moving forward with the flow, and thus become concentrated. In one embodiment, the detection site is upstream away from the electrodes.

Figure 6:
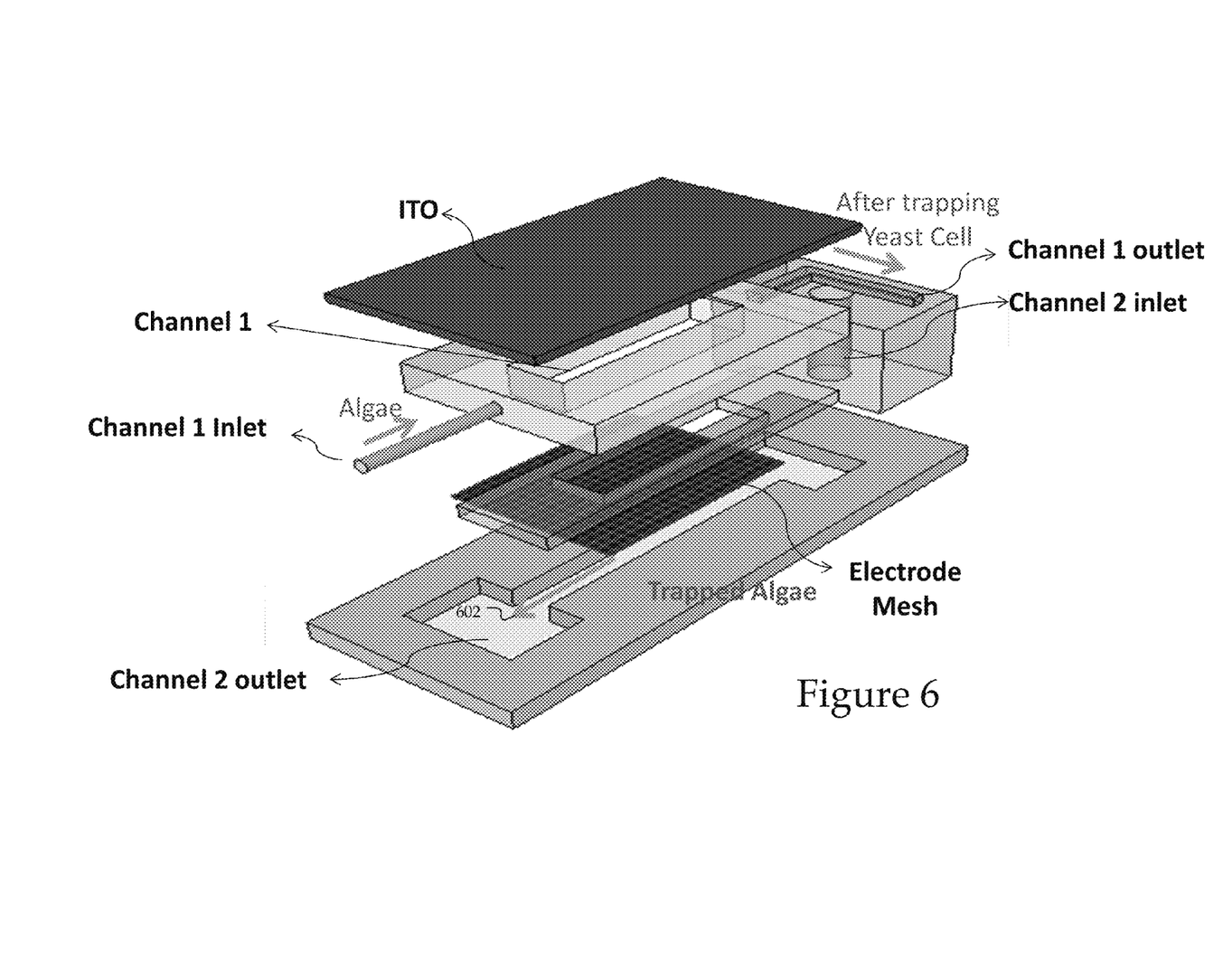
FIG. 6 is a schematic of a sample trapping system.

FIG. 6 is a schematic of an algae trapping system. Although not shown in FIG. 3, there may be two sets of channels as illustrated in FIG. 6. FIG. 6 illustrates the inlets and outlets for two channels, Channel 1 and Channel 2. The flow of the algae is shown from the Channel 1 inlet and the flow of the algae through the Channel 2 outlet 602. The electrode mesh is located between Channel 2 and the sample area. The electrode mesh may act as one electrode while the ITO glass slide acts as another electrode. When a voltage is applied between the ITO slide and the mesh, there may be an inhomogeneous electric field around the mesh electrode, which may induce downwards fluid movement (by principles of AC electroosmosis and AC electrothermal effect) through the mesh. As a result, the particles (algae) may be carried into channel 2, where they may be trapped. The upper layer may be another electrode 704 facing the mesh electrode (an indium tin oxide ("ITO") layer used here for observing the algae) that is adjacent to Channel 1. The upper layer may be made of another material. For example, other transparent conducting oxides may be used because of their electrical conductivity and optical transparency, as well as the ease with which they can be deposited as a thin film. If the photodetector is incorporated through the bottom of channel 2, then the top electrode does not need to be transparent. The design of the channels allows for particle accumulation, but also allows for particle release and delivery. In other words, the particles are not accumulated permanently and can be washed after analysis.

Figure 7:
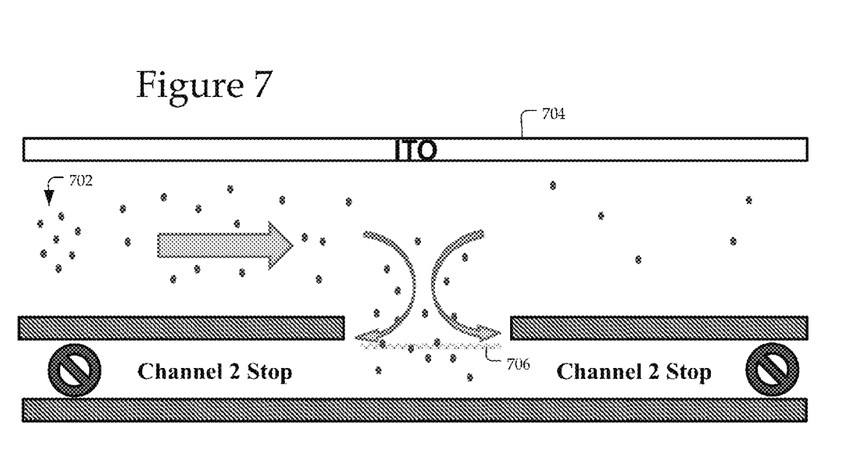
FIG. 7 is a diagram of particle trapping in a first channel.

FIG. 7 is a diagram of particle trapping in a first channel. The particles 702 travel along the first channel which is the upper channel adjacent to the ITO layer 704. Channel 1 is connected to the environment and passed with a continuous flow to supply particles, while Channel 2 is for the retaining and release of those particles. FIG. 7 illustrates the directing particles from Channel 1 to Channel 2 and trapping particles in Channel 2 when Channel 2 is stopped. The particles 702 flow through the mesh electrode 706. The mesh electrode 706 stops particles from getting back into Channel 1. The algae sample is pumped through the channel from left to right. By applying the electricity, the algae may be convected into Channel 2 through the mesh electrode 706 because of microflows induced by AC electroosmosis and AC electrothermal effect. An accompanying AC electrokinetic effect, dielectrophoresis (DEP), determines the AC frequency to be used. Negative DEP repels particles from the electrodes. Negative DEP may be induced here so as to avoid the trapping of particles onto the electrodes. Even though negative DEP deters the particle movement towards Channel 2, once the particles reach Channel 2, the negative DEP may prevent their return to Channel 1.

Figure 8:
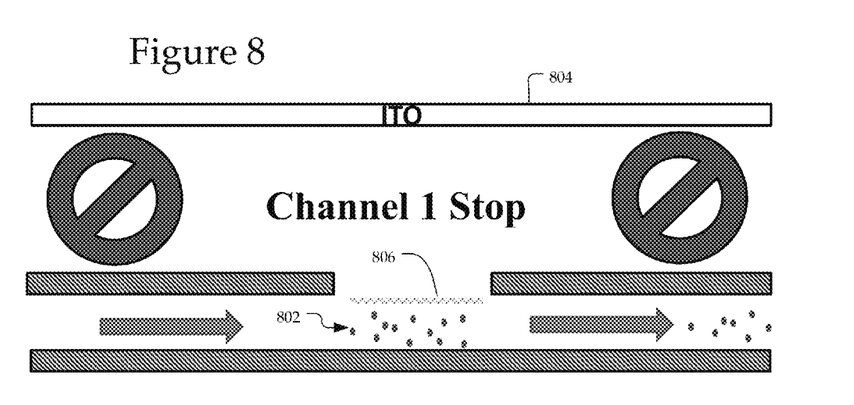
FIG. 8 is a diagram of particle releasing in a second channel.

FIG. 8 is a diagram of particle releasing in a second channel. The particles 802 travel along the second channel which is the lower channel. In particular, Channel 1 is for the supply of particles and Channel 2 is for the trapping and release of particles. FIG. 8 illustrates the release of particles in Channel 2. Channel 1 is adjacent to the ITO layer 804 and is stopped. The mesh electrode 806 may serve a similar function as with the mesh electrode 706 in FIG. 7. Mesh electrode 806 may be turned off so that the particles flow through Channel 2 for release. The heights of the channels and/or the size of the gap for the mesh electrode 806 may be modified for improved trapping. However, improved trapping may decrease the ability to release the particles. For example, a smaller gap size may improve trapping but make particle release more difficult. Likewise, the flow rate may be modified for improved trapping and/or improved particle release.

Figure 9:
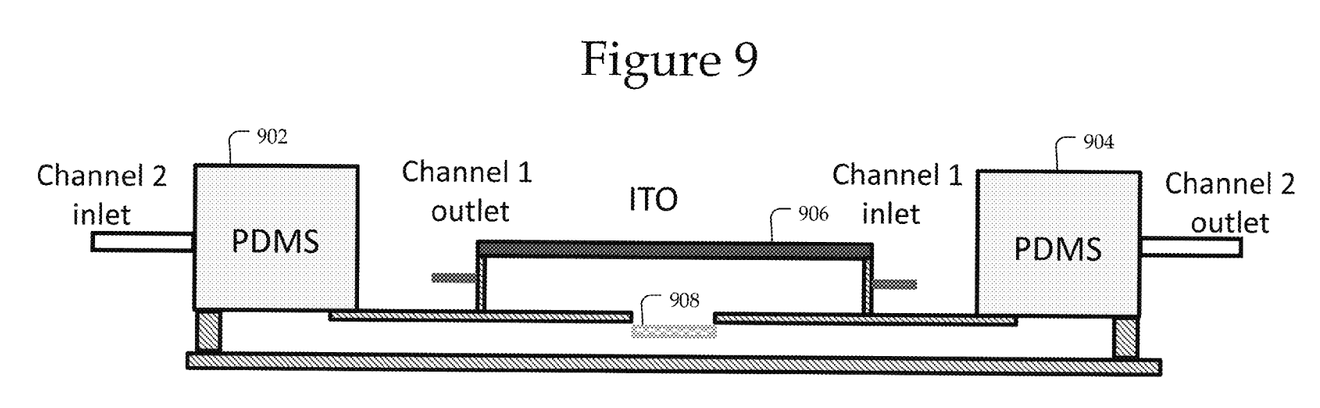
FIG. 9 is a diagram of the channel structure for a trapping device.

FIG. 9 is a diagram of the channel structure for a trapping device. The two channels are illustrated with both inlets and outlets. There is a Polydimethylsiloxane (PDMS) 902 at the channel 2 inlet and a PDMS 904 at the channel 2 outlet. PDMS or Polydimethylsiloxane belongs to a group of polymeric organosilicon compounds that are commonly referred to as silicones. PDMS is a silicon-based organic polymer, and is known for its unusual rheological (or flow) properties. PDMS is optically clear and is considered to be inert, non-toxic and non-flammable. PDMS 902 and 904 are interconnects made from PDMS. There may be hollow channels in 902 and 94 that connect tubes from an external pump to microchannels. There may be a cover to the channels, such as ITO 906. The mesh electrode 908 that separates the channels may be similar to the mesh electrodes described with respect to FIGS. 7-8.

Figure 10:
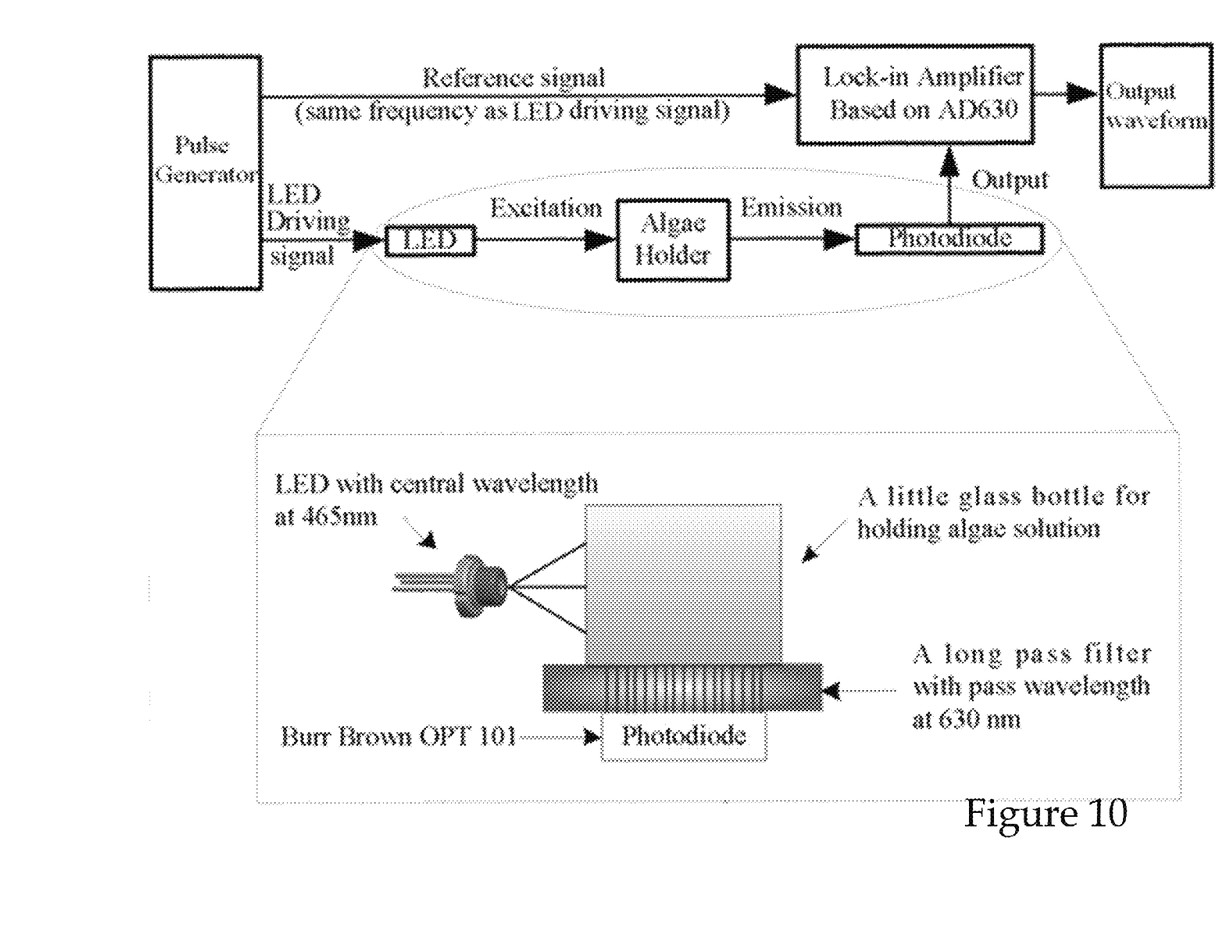
FIG. 10 is an embodiment of the LOAC PAM fluorometer with a single light source.

FIG. 10 is an embodiment of the LOAC PAM fluorometer with a single light source. In particular, FIG. 10 is a board-level system diagram illustrating an LOAC PAM with a single light source (LED). In particular, one LED (e.g. Blue 30° 5 mm LED with a center wavelength of approximately 465 nm) may be provided for both the measuring and actinic light. The LED may be driven by a signal generator (e.g. Model 8551, 50 MHz Single-Channel PLL Pulse Function Generator, Tabor Electronics, Israel). Different light intensity for the measuring light and actinic light may be realized by adjusting the voltage supplied to the LED drive. The voltage that powered the LED may be adjusted sequentially as follows, 1.8V-2.0V-9.0V-2.0V-1.8V, with 1.8V is below the turn-on voltage for the LED, corresponding to an "off" state. 2.0V may be barely over the LED turn-on voltage and corresponds to the measuring light intensity, and 9.0V may correspond to the actinic light. Fluorescent light emitted by algae will pass through a long pass filter with a pass wavelength at 630 nm and become collected by a photodiode (e.g. OPT101, Texas Instrument, Inc.). Subsequently, a lock-in amplifier may amplify the output voltage from the photodiode and remove its carrier frequency component.

Figure 11:
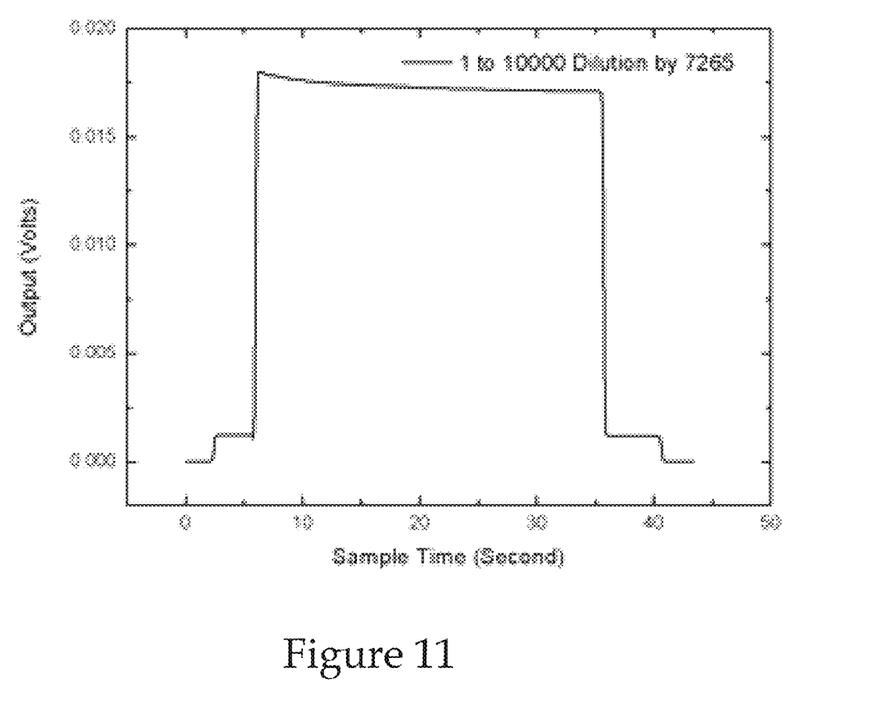
FIG. 11 is a representation of voltage data out of a lock-in amplifier when an algae sample being excited with light.

FIG. 11 is a representation of voltage data out of a lock-in amplifier when an algae sample being excited with light. In particular, FIG. 11 illustrates time-dependent fluorescence induction signals for the green algae Chlamydomonas diluted to 0.1269355 ug/L. The voltage data out of a lock in amplifier that is measured may be when an algae sample being excited with measuring light and/or actinic light. From 0-2 seconds, the LED at 1.8V or below is off. From 2-6 seconds, the LED at 2V provides a pulsed measuring light. From 6-35 seconds, the LED at 9V provides an actinic light of the same pulsed frequency. From 35-40 seconds, the LED is again at 2V and provides a measuring light. After 40 seconds, the LED is off.

The system and process described may be encoded in a signal bearing medium, a computer readable medium such as a memory, programmed within a device such as one or more integrated circuits, and one or more processors or processed by a controller or a computer. If the methods are performed by software, the software may reside in a memory resident to or interfaced to a storage device, synchronizer, a communication interface, or non-volatile or volatile memory in communication with a transmitter. A circuit or electronic device designed to send data to another location. The memory may include an ordered listing of executable instructions for implementing logical functions. A logical function or any system element described may be implemented through optic circuitry, digital circuitry, through source code, through analog circuitry, through an analog source such as an analog electrical, audio, or video signal or a combination. The software may be embodied in any computer-readable or signal-bearing medium, for use by, or in connection with an instruction executable system, apparatus, or device. Such a system may include a computer-based system, a processor-containing system, or another system that may selectively fetch instructions from an instruction executable system, apparatus, or device that may also execute instructions.

A "computer-readable medium," "machine readable medium," "propagated-signal" medium, and/or "signal-bearing medium" may comprise any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

We claim:

1. A system for chlorophyll fluorometry comprising:
    a trapping device for trapping particles from a sample in a fluid, the trapping device comprising: a first fluidic channel including a first inlet and a first outlet, a second fluidic channel including a second inlet and a second outlet, a gap between the first channel and the second channel and electrodes for controlling movement of the particles in the fluid from the first fluidic channel to the second fluidic channel through the gap, wherein at least a portion of one or of both of the first fluidic channel and the second fluidic channel is transparent; and
    a pulse amplitude modulated (PAM) light source positioned over the transparent portion of one or both of the first fluidic channel and the second fluidic channel, wherein the light source emits pulse amplitude modulated light through the transparent portion of one or both of the first fluidic channel and the second fluidic channel onto the trapped particles in the fluid;
    a pulse signal generator that pulse amplitude modulates the emitted light on the trapped particles in the fluid; and
    a photodetector that detects chlorophyll fluorometry changes in the trapped particles in the fluid from the pulse amplitude modulated emitted light.

2. The system of claim 1 wherein the trapping device comprises the first fluidic channel and the second fluidic channel for transporting the sample in the fluid.

3. The system of claim 2 wherein the first fluidic channel comprises a trapping channel for trapping the particles in the fluid from the sample and the second fluidic channel comprises a release channel for releasing the trapped particles in the fluid.

4. The system of claim 3 wherein at least one electrode coupled with the first fluidic channel establishes the trapping of the particles in the fluid.

5. The system of claim 4 wherein the first fluidic channel concentrates the particles in the fluid for being subject to the emitted light.

6. The system of claim 4 wherein the releasing of the trapped particles in the fluid is established by not providing a current to the at least one electrode.

7. The system of claim 2 wherein the trapping device comprises two layers of channels, wherein the first fluidic channel is an upper layer and the second fluidic channel is a lower layer.

8. The system of claim 1 further comprising a computer coupled with the photodetector for analyzing the detected changes.

9. The system of claim 1 wherein the light source comprises at least two light emitting diodes (LEDs).

10. The system of claim 1 further comprising a lab on a chip design in which the system is embodied on a single chip.

11. The system of claim 1 further comprising a computer coupled with the photodetector, the computer utilized for analyzing the detected changes, wherein the analysis identifies toxin in the sample.

12. A chlorophyll fluorometer apparatus comprising:
a first fluidic channel for concentrating particles from a sample in a fluid for measurement;
at least one light source using pulse amplitude modulation (PAM) for illuminating the concentrated particles in the fluid; and
a photodetector that detects chlorophyll signatures of the particles in the fluid upon the illumination of the particles in the fluid by the light source using pulse amplitude modulation;
wherein the at least one light source using pulse amplitude modulation (PAM) for illuminating the concentrated particles in the fluid, is pulsed such that it mimics two light sources including a dimmer steady state light and a brighter PAM actinic light.

13. The apparatus of claim 12 wherein wherein the first fluidic channel comprises a fluidic meandering channel.

14. The apparatus of claim 13 wherein the first fluidic channel traps the particles in the fluid for concentration and the second fluidic channel releases the particles in the fluid from being trapped.

15. The apparatus of claim 13 wherein the first fluidic channel is coupled with at least one electrode for concentrating the particles in the fluid when the electrode is activated.

16. The apparatus of claim 15 wherein a second fluidic channel releases the concentrated particles in the fluid when the electrode is deactivated.

17. The apparatus of claim 12 further comprising a pulse signal generator that pulse amplitude modulates emissions form the at least one source that result in the PAM emissions.

18. The apparatus of claim 12 further comprising a computer coupled with the photodetector, wherein the computer is utilized for analyzing the detected changes.

19. The apparatus of claim 12 wherein the at least one light source comprises at least two light emitting diodes (LEDs).

20. The apparatus of claim 12 further comprising a lab on a chip design in which the chlorophyll fluorometer is embodied on a single chip.

21. A method for chlorophyll fluorometry comprising:
trapping particles from a sample in a fluid in a first fluidic channel that comprises a first inlet and a first outlet;
emitting a signal onto the trapped particles in the fluid;
detecting changes in the chlorophyll fluorometry of the particles in the fluid;
analyzing the detected changes for identifying toxins in the sample;
moving the particles in the fluid from the first fluidic channel to a second fluidic channel through a gap between the first fluidic channel and the second fluidic channel utilizing electrodes; and
releasing the trapped particles in the fluid through the second fluidic channel that comprises a second inlet and a second outlet.

22. The system of claim 1, wherein one or both of the first fluidic channel and the second fluidic channel comprise a fluidic meandering channel.

\* \* \* \* \*

UNITED STATES PATENT AND TRADEMARK OFFICE
CERTIFICATE OF CORRECTION

PATENT NO. : 9,222,888 B2  Page 1 of 1
APPLICATION NO. : 13/438562
DATED : December 29, 2015
INVENTOR(S) : Elias Greenbaum et al.

It is certified that error appears in the above-identified patent and that said Letters Patent is hereby corrected as shown below:

In the Claims

In column 11, claim 13, line 37, after "of claim 12" delete "wherein" (first occurrence).

Signed and Sealed this
Nineteenth Day of April, 2016

Michelle K. Lee
*Director of the United States Patent and Trademark Office*